(12) United States Patent
Matsuura et al.

(10) Patent No.: US 6,649,180 B1
(45) Date of Patent: Nov. 18, 2003

(54) HARD CAPSULE FORMED OF CELLULOSE ETHER FILM WITH A SPECIFIC CONTENT OF METHOXYL AND HYDROXYPROPOXYL GROUPS

(75) Inventors: Seinosuke Matsuura, Kyoto (JP); Masaru Tanjoh, Sakurai (JP)

(73) Assignee: Shionogi Qualicaps Co., Ltd., Yamatokoriyama (JP)

( * ) Notice: Subject to any disclaimer, the term of this patent is extended or adjusted under 35 U.S.C. 154(b) by 0 days.

(21) Appl. No.: 09/549,205

(22) Filed: Apr. 13, 2000

(30) Foreign Application Priority Data

Apr. 14, 1999 (JP) .............................. 11-106689

(51) Int. Cl.$^7$ ............................... B29D 22/00
(52) U.S. Cl. ...................... 424/402; 424/403; 424/451; 428/34.3; 428/532
(58) Field of Search ................. 424/435, 436, 424/451, 452, 455, 456, 463, DIG. 15, 402, 403; 428/34.3, 532

(56) References Cited

U.S. PATENT DOCUMENTS

| 4,365,060 A | * | 12/1982 | Onda et al. ................ 536/65 |
| 5,431,917 A | * | 7/1995 | Yamamoto et al. ......... 424/451 |
| 5,431,919 A | | 7/1995 | Maruyama et al. ......... 424/473 |
| 6,228,416 B1 | * | 5/2001 | Reibert et al. ............. 426/573 |
| 6,326,026 B1 | * | 12/2001 | Parekh et al. .............. 424/451 |

FOREIGN PATENT DOCUMENTS

| EP | 0592130 A2 | 4/1994 |
| EP | 0714656 A1 | 6/1996 |
| JP | B2-2552937 | 8/1996 |
| WO | 9827151 A1 | 6/1998 |

* cited by examiner

*Primary Examiner*—Paul Thibodeau
*Assistant Examiner*—Kevin M. Bernatz
(74) *Attorney, Agent, or Firm*—Birch, Stewart, Kolasch & Birch, LLP

(57) ABSTRACT

A cellulose ether film is formed of a composition comprising a cellulose ether as a base in which some of the hydrogen atoms of cellulosic hydroxyl groups are replaced by alkyl groups and/or hydroxyalkyl groups, a gelling agent, and a gelling aid. The total content of alkoxyl and hydroxyalkoxyl groups in the cellulose ether is limited to 23–37.6% by weight, which is effective for preventing the gelling aid from precipitating out and maintaining a favorable outer appearance during long-term storage.

5 Claims, No Drawings

HARD CAPSULE FORMED OF CELLULOSE ETHER FILM WITH A SPECIFIC CONTENT OF METHOXYL AND HYDROXYPROPOXYL GROUPS

This invention relates to a cellulose ether film suited for use in forming pharmaceutical and food hard capsules.

BACKGROUND OF THE INVENTION

Hard capsules are commonly used in the pharmaceutical and health food fields. Of the hard capsules, gelatin capsules are most widely used. They are formed from a film of a composition comprising gelatin as a base, a plasticizer (e.g., glycerin or sorbitol), opacifying agent, dye, pigment, and other addenda. Typically, gelatin capsules are manufactured by dipping pins in an aqueous gelatin solution having the above components blended, drawing out the pins with the aqueous gelatin solution adhering to the pins, and drying the gelatin coats.

Flexibility and other properties of gelatin-based film largely depend on the water content of the film. A film with a low water content is too low in impact resistance to withstand the shocks encountered upon filling of medicament. Also, as the water content decreases by drying during storage, the film contracts to undesirably loosen the cap-to-body engagement. To prevent such inconvenience, gelatin capsules must be kept at an optimum water content of about 13 to 15% by weight. Because of the necessity to have such a relatively high water content, it is restricted to apply the gelatin capsules to those medicaments which give rise to a problem upon contact with water. When the gelatin capsules contain a hygroscopic fill, the capsules gradually lose the water content and hence, the strength, inviting the risk of failure.

Under the circumstances, studies have been made on the capsules which can avoid the problems associated with water contents and which are applicable to any type of fill. One exemplary substitute for the gelatin capsules is capsules whose film is formed of a cellulose ether composition comprising a water-soluble cellulose ether as a base in which some of the hydrogen atoms of cellulosic hydroxyl groups are replaced by alkyl and hydroxyalkyl groups or hydroxyalkyl groups, a gelling agent, and a gelling aid, as disclosed in Japanese Patent No. 2,552,937. Some capsules based on hydroxypropyl methyl cellulose (HPMC) have been used in practice. These capsules of cellulose ether film maintain a sufficient strength even at a low water content, and their behaviors such as dissolution are equivalent to those of conventional gelatin capsules. Additionally, they can be manufactured by the so-called dipping method as are conventional gelatin capsules.

However, the capsules of cellulose ether film suffer from the problem that the gelling aid which is blended for assisting in film formation will precipitate out on the film surface during long-term storage.

More particularly, in one appropriate formulation of the cellulose ether film for forming capsules, carrageenan is used as a gelling agent for HPMC, and a potassium or calcium ion is incorporated as a gelling aid in the form of a water-soluble compound such as potassium chloride or calcium chloride. During long-term storage of these cellulose ether film capsules, the water content of the film can be lowered owing to the storage environment or the water absorption of the fill. Then the potassium or calcium ion as the gelling aid will re-form potassium chloride or calcium chloride which precipitates out on the film surface.

The precipitates of the gelling aid give rise to no problem to the practical usage, but are unpleasant to look at. Especially in the case of colorless clear film, the precipitates develop as cloud and sometimes, cloud spots rather than uniform cloud, exacerbating the outer appearance of capsules noticeably.

SUMMARY OF THE INVENTION

An object of the invention is to provide a novel and improved cellulose ether film of a composition comprising a cellulose ether as a base, a gelling agent, and a gelling aid, which prevents the gelling aid from precipitating out and maintains a favorable outer appearance during long-term storage.

It has been found that when a film, typically a capsule film is formed of a composition comprising a cellulose ether as a base in which some of the hydrogen atoms of cellulosic hydroxyl groups are replaced by alkyl groups and/or hydroxyalkyl groups, a gelling agent, and a gelling aid, the use of the cellulose ether having an alkoxyl and hydroxyalkoxyl content of up to 37.6% by weight is effective for preventing precipitation of the gelling aid, thereby maintaining a favorable outer appearance even after long-term storage.

Accordingly, the invention provides a cellulose ether film formed of a composition comprising a cellulose ether as a base in which some of the hydrogen atoms of cellulosic hydroxyl groups are replaced by alkyl groups and/or hydroxyalkyl groups, a gelling agent, and a gelling aid, wherein the total content of alkoxyl and hydroxyalkoxyl groups in the cellulose ether is up to 37.6% by weight.

Although the reason why precipitation of the gelling aid can be restrained by limiting the total content of alkoxyl and hydroxyalkoxyl groups in the cellulose ether to 37.6% by weight or lower is not well understood, the following mechanism is inferred. In the cellulose ether used as the film base, some of the hydrogen atoms of cellulosic hydroxyl groups are replaced by alkyl groups and/or hydroxyalkyl groups whereby the hydroxyl groups are converted into alkoxyl or hydroxyalkoxyl groups. By limiting the total content of alkoxyl and hydroxyalkoxyl groups to 37.6% by weight or lower, the proportion of (remaining) hydroxyl groups having high affinity to water becomes relatively high so that the water-holding force of the film is effectively improved. This ensures that potassium or calcium as the gelling aid is retained in ion form within the water held in the film, effectively restraining precipitation of the gelling aid.

DESCRIPTION OF THE PREFERRED EMBODIMENT

Briefly stated, the cellulose ether film of the invention is manufactured by using a cellulose ether as a base, blending a gelling agent and a gelling aid therein, and forming the composition into a film.

The cellulose ether used as the base is one in which some of the hydrogen atoms of cellulosic hydroxyl groups are replaced by alkyl groups and/or hydroxyalkyl groups whereby alkoxyl and/or hydroxyalkoxyl groups are created.

Though not critical, the cellulose ether is preferably one in which some of the hydrogen atoms of cellulosic hydroxyl groups are replaced by alkyl groups and hydroxyalkyl groups or by only hydroxyalkoxyl groups. Of the alkyl groups, methyl is preferred. Of the hydroxyalkyl groups, hydroxypropyl or hydroxyethyl is preferred. Illustrative examples of the cellulose ether substituted with these groups include hydroxypropyl methyl cellulose (HPMC), hydroxypropyl cellulose (HPC), hydroxyethyl methyl cellulose (HEMC), and methyl cellulose (MC). Of these, HPMC is best suited for capsule film application because of effective film formation and mechanical strength at low water contents.

According to the invention, the total content of alkoxyl and hydroxyalkoxyl groups created in the cellulose ether by introducing the above substituents is limited to 37.6% by weight or lower. More particularly, the total content corresponds to the total content of methoxyl groups (abbreviated as "MO groups") and hydroxypropoxyl groups (abbreviated as "HPO groups") in the case of HPMC, the content of HPO groups in the case of HPC, the total content of MO groups and hydroxyethoxyl groups in the case of HEMC, and the content of MO groups in the case of MC. A cellulose ether having a total content of such substituents of up to 37.6% by weight is used.

The lower the total content of alkoxyl and hydroxyalkoxyl groups, the better becomes the effect of preventing precipitation of the gelling aid. However, if the total content of alkoxyl and hydroxyalkoxyl groups is too low, the resulting film may lose flexibility, strength or other performance, which is inconvenient in some applications. Therefore, the total content of alkoxyl and hydroxyalkoxyl groups is preferably in the range of 23 to 37.6% by weight though not limited thereto. Especially when the film is used as capsule shells, the total content of alkoxyl and hydroxyalkoxyl groups is preferably in the range of 29 to 37% by weight for finding a good compromise between the film strength and the effect of preventing precipitation of the gelling aid.

Of the above-described cellulose ethers, HPMC, HPC, and MC are specified in the Pharmacopoeia of Japan. In the capsule shell application, it is recommended to use the pharmacopoeia-specified products.

For HPMC, the Pharmacopoeia specifies three types, hydroxypropyl methyl cellulose 2208, hydroxypropyl methyl cellulose 2906, and hydroxypropyl methyl cellulose 2910, depending on the contents of MO and HPO groups. It is specified that hydroxypropyl methyl cellulose 2208 contains 19 to 24 wt % of MO groups and 4 to 12 wt % of HPO groups in a total of 23 to 36 wt %; hydroxypropyl methyl cellulose 2906 contains 27 to 30 wt % of MO groups and 4 to 7.5 wt % of HPO groups in a total of 31 to 37.5 wt %, and hydroxypropyl methyl cellulose 2910 contains 28 to 30 wt % of MO groups and 7 to 12 wt % of HPO groups in a total of 35 to 42 wt %. Any of these celluloses may be used in the practice of the invention as long as the total content of MO and HPO groups is up to 37.6 wt %. Also acceptable are mixtures in which any two or more of these celluloses are mixed to adjust the total content of MO and HPO groups to that range.

It is noted that the contents of alkoxyl and hydroxyalkoxyl groups in cellulose ether can be determined by the measurement method described in the Pharmacopoeia for the HPMC, HPC and MC specified therein, and by a well-known method for the remaining cellulose ethers.

The gelling agent used may be selected from among, for example, carrageenan, tamarind seed polysaccharide, pectin, curdlan, furcellaran, gellan gum, and mixtures thereof. Of these, carrageenan is especially preferred because it has a high gel strength and exhibits good gelling properties in the co-presence of a specific ion so that it may achieve effective gelation even when added in small amounts. While there are known three types: kappa-carrageenan or iota-carrageenan and lambda-carrageenan, the invention recommends to use kappa-carrageenan and/or iota-carrageenan which have a good gelation ability.

The amount of the gelling agent used is not critical and may be suitably determined in accordance with the type of cellulose ether and gelling agent, the intended application of film, and film forming method. When capsule shells are formed by the well-known dipping method, for example, it is recommended to use about 0.05 to 25 parts, and especially about 0.25 to 15 parts by weight of the gelling agent per 100 parts by weight of the cellulose ether. Less than 0.05 part of the gelling agent may achieve a lower degree of gelation and fail to produce a film of a sufficient thickness to enable shell formation by the dipping method. More than 25 parts of the gelling agent may achieve a too high degree of gelation and provide a dipping solution with a viscosity higher than necessity, making it difficult to form a uniform coat or film.

As the gelling aid used herein, any substance that can promote gelation by the gelling agent may be employed. Depending on the type of the gelling agent, the gelling aid may be selected from a potassium ion, calcium ion, ammonium ion, and various organic compounds which can promote gelation by the gelling agent. Especially when capsule shells are formed using carrageenan as the gelling agent, a potassium ion or calcium ion or both are preferably used. The potassium ion may be blended in the form of its water-soluble compound such as potassium chloride, potassium phosphate or potassium citrate. The calcium ion may be blended in the form of its water-soluble compound such as calcium chloride.

Like the gelling agent, the amount of the gelling aid used is not critical and may be suitably determined in accordance with the type of cellulose ether and gelling agent, the intended application of film, and film forming method. When capsule shells are formed by the well-known dipping method, for example, it is recommended to use about 0.05 to 25 parts, and especially about 0.25 to 15 parts by weight, calculated as ion, of the gelling aid per 100 parts by weight of the cellulose ether. Less than 0.05 part of the gelling aid may promote gelation of the gelling agent to a less extent and fail to produce a film of a sufficient thickness to enable shell formation by the dipping method. More than 25 parts of the gelling aid may form a gel in a dipping solution for rendering it difficult to form a film, and in addition, adversely affect the disintegration (i.e., dissolution after administration) of the resulting film, which is inconvenient as the capsule shells.

While the cellulose ether film of the invention contains the cellulose ether as the base, the gelling agent and the gelling aid, there may be added appropriate amounts of various additives including coloring agents such as dyes and pigments, opacifying agents, and perfumes.

The cellulose ether film can be manufactured by any well-known method depending on its application. When hard capsules are formed from the cellulose ether film of the invention, for example, the film can be prepared in the form of capsule shells by a well-known dipping method as in the manufacture of conventional gelatin capsules. In one exemplary process, the cellulose ether, gelling agent, gelling aid and optional additives are dissolved in water in appropriate amounts as mentioned above to form a dipping solution, capsule-forming pins are dipped in the dipping solution, then drawn out of the solution. The solution adhering to the outside surface of the pins is dried to form capsule shells (caps or bodies) on the outside surface of the pins whereupon the shells are removed from the pins. In this way, the cellulose ether film of the invention is obtained in the form of capsule shells. The shells are then cut to a predetermined size and mated to construct hard capsules of the cellulose ether film according to the invention.

As mentioned above, the dipping solution is an aqueous solution having predetermined amounts of the cellulose ether, gelling agent, gelling aid and optional additives blended therein. This aqueous solution is preferably prepared to a concentration of 15 to 30% by weight, and especially 18 to 25% by weight of the cellulose ether. Less than 15% by weight of the cellulose ether may fail to form a film of a sufficient thickness to serve as capsule shells whereas more than 30% by weight of the cellulose ether may provide the dipping solution with too high a viscosity to form a uniform film. The remaining conditions may be the same as those customarily used in the manufacture of cellulose ether-based capsules.

The cellulose ether film of the invention is suitable as the shell of hard capsules for use in the pharmaceutical and health food fields although the application is not limited thereto. The film may find use in applications other than hard capsules.

EXAMPLE

Examples of the invention are given below by way of illustration and not by way of limitation.

Hydroxypropyl methyl cellulose 2910 specified in the Pharmacopoeia of Japan ("Metolose 60SH" by Shin-Etsu Chemical Co., Ltd.) and hydroxypropyl methyl cellulose 2208 ("Metolose 90SH" by Shin-Etsu Chemical Co., Ltd.) were mixed in the proportion shown in Table 1. Using this hydroxypropyl methyl cellulose, a dipping solution of the composition shown below was prepared. By a conventional dipping method, size No. 2 hard capsules of colorless clear hydroxypropyl methyl cellulose film of about 100 microns thick were prepared therefrom.

Note that the contents of methoxyl and hydroxypropoxyl groups in hydroxypropyl methyl cellulose 2910 (Metolose 60SH) and hydroxypropyl methyl cellulose 2208 (Metolose 90SH) were determined by the measurement method prescribed in the Pharmacopoeia of Japan, with the results shown below.

2910 (60SH) —$OCH_3$: 28.8%, —$OC_3H_6OH$: 9.3%, total: 38.1%

2208 (90SH)

—$OCH_3$: 23.5%, —$OC_3H_6OH$: 5.9%, total: 29.4%

Dipping Solution Composition

| | |
|---|---|
| Hydroxypropyl methyl cellulose | 20 wt % |
| κ-carrageenan (gelling agent) | 0.1 wt % |
| Potassium chloride (gelling aid) | 0.1 wt % |
| | (0.052 wt % of $K^+$) |
| Water | balance |

The capsules thus obtained were contained in a glass bottle and stored at 40° C. for one month. The capsule surface was visually observed to inspect precipitates of potassium chloride thereon. The results are shown in Table 1.

TABLE 1

| | Cellulose mixture of 2910:2208 (weight ratio) | Total content of $OCH_3$ + $OC_3H_6OH$ (wt %) | Precipitation of KCl on capsule surface (40° C., 1 month in glass bottle) |
|---|---|---|---|
| Comparison | 100:0 | 38.1% | precipitates, locally look white |
| Example 1 | 95:5 | 37.6% | a few precipitates, but acceptable outer appearance |
| Example 2 | 80:20 | 36.4% | no precipitates |
| Example 3 | 70:30 | 35.5% | no precipitates |
| Example 4 | 0:100 | 29.4% | no precipitates |

As seen from Table 1, controlling the total content of alkoxyl and hydroxyalkoxyl groups in the cellulose ether to 37.6% by weight or lower is effective for preventing the gelling aid (potassium chloride in these examples) from precipitating on the film surface.

There has been described a cellulose ether film in which the cellulose ether used as the base has an optimum content of alkoxyl and hydroxyalkoxyl groups, which is effective for preventing the gelling aid from precipitating out and maintaining a favorable outer appearance during long-term storage. The cellulose ether film is thus suitable as the shell of hard capsules for use in the pharmaceutical and health food fields.

Japanese Patent Application No. 11-106689 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A hard capsule formed of a film composition comprising a hydroxypropyl methyl cellulose as a base, a gelling agent, and a gelling aid, wherein said hydroxypropyl methyl cellulose has a content of hydroxypropoxyl groups of at least 4% by weight of the hydroxypropyl methyl cellulose and a content of methoxyl groups and hydroxypropoxyl groups combined of 23 to 37.6% by weight of the hydroxypropyl methyl cellulose.

2. The hard capsule formed of a film of claim 1, wherein said composition contains 100 parts by weight of the hydroxypropyl methyl cellulose, 0.05 to 25 parts by weight of the gelling agent, and 0.05 to 25 parts by weight of the gelling aid.

3. The hard capsule formed of a film of claim 1, wherein the gelling agent is selected from the group consisting of carrageenan, tamarind seed polysaccharide, pectin, curdlan, furcellaran, gellan gum, and mixtures thereof.

4. The hard capsule formed of a film of claim 1, wherein the content of methoxyl and hydroxypropoxyl groups combined is 29 to 37% by weight of the hydroxypropyl methyl cellulose.

5. The hard capsule formed of a film of claim 1 or 4, wherein the gelling aid is selected from the group consisting of a potassium ion, calcium ion, ammonium ion, and mixtures thereof.

* * * * *